(12) United States Patent
Beden et al.

(10) Patent No.: US 9,186,451 B2
(45) Date of Patent: Nov. 17, 2015

(54) METHOD AS WELL AS APPARATUSES FOR RETROGRADE FILLING OF AT LEAST ONE CALCIUM LINE OF AN EXTRACORPOREAL BLOOD CIRCUIT

(71) Applicants: Josef Beden, Mainz-Kastel (DE); Olaf Kessel-Deynet, Zell (DE); Juergen Klewinghaus, Oberursel (DE); Thomas Pusinelli, Altenstadt (DE); Pascal Werner, Uechtelhausen (DE)

(72) Inventors: Josef Beden, Mainz-Kastel (DE); Olaf Kessel-Deynet, Zell (DE); Juergen Klewinghaus, Oberursel (DE); Thomas Pusinelli, Altenstadt (DE); Pascal Werner, Uechtelhausen (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 430 days.

(21) Appl. No.: 13/654,519

(22) Filed: Oct. 18, 2012

(65) Prior Publication Data

US 2013/0098838 A1    Apr. 25, 2013

Related U.S. Application Data

(60) Provisional application No. 61/548,745, filed on Oct. 19, 2011.

(30) Foreign Application Priority Data

Oct. 19, 2011   (DE) .......................... 10 2011 116 262

(51) Int. Cl.
*A61M 1/14* (2006.01)
*A61M 1/34* (2006.01)
*A61M 1/36* (2006.01)

(52) U.S. Cl.
CPC ........... *A61M 1/3643* (2013.01); *A61M 1/3437* (2014.02); *A61M 1/3455* (2013.01); *A61M 1/3458* (2014.02); *A61M 1/3624* (2013.01); *A61M 1/3675* (2013.01); *A61M 2205/3382* (2013.01)

(58) Field of Classification Search
CPC ............ A61M 1/3643; A61M 1/3624; A61M 1/3437; A61M 1/3455; A61M 1/3458; A61M 1/3675; A61M 2205/3382
See application file for complete search history.

(56) References Cited

U.S. PATENT DOCUMENTS

2004/0195178 A1   10/2004   Carpenter et al.
2008/0015487 A1   1/2008    Szamosfalvi (Continued)

FOREIGN PATENT DOCUMENTS

DE   197 04 564 A1   8/1998
DE   100 11 208 C1   9/2001

(Continued)

OTHER PUBLICATIONS

PCT International Search Report from PCT/EP2012/004351, mailed on Jan. 21, 2013.

*Primary Examiner* — John Kim
(74) *Attorney, Agent, or Firm* — Kenyon & Kenyon LLP

(57) ABSTRACT

The present invention relates to a method for priming a line for adding a medical solution, the line branching off a return line of an extracorporeal blood circuit, in particular a calcium line, a control device for controlling or regulating the method according to the present invention and a blood or plasma treatment apparatus with at least the control device according to the present invention. It further relates to a digital storage medium, a computer program product as well as a computer program.

13 Claims, 3 Drawing Sheets

(56) References Cited

U.S. PATENT DOCUMENTS

| | | |
|---|---|---|
| 2009/0114593 A1 | 5/2009 | Fischer |
| 2009/0221948 A1 | 9/2009 | Szamosfalvi et al. |
| 2010/0004579 A1 | 1/2010 | Kopperschmidt |
| 2010/0049115 A1 | 2/2010 | Biesel et al. |
| 2011/0237997 A1* | 9/2011 | Beden et al. ............ 604/6.09 |
| 2012/0000547 A1 | 1/2012 | Gronau et al. |

FOREIGN PATENT DOCUMENTS

| | | |
|---|---|---|
| DE | 10 2006 022122 A1 | 11/2007 |
| DE | 102006039675 A1 | 2/2008 |
| DE | 10 2006 061184 A1 | 6/2008 |
| DE | 10 2009 008346 A1 | 8/2010 |
| WO | 99/37335 A1 | 7/1999 |
| WO | 2009044221 A1 | 4/2009 |

* cited by examiner

METHOD AS WELL AS APPARATUSES FOR RETROGRADE FILLING OF AT LEAST ONE CALCIUM LINE OF AN EXTRACORPOREAL BLOOD CIRCUIT

CROSS REFERENCE TO RELATED APPLICATIONS

This application claims the benefit of U.S. Provisional Patent Application No. 61/548,745 filed on Oct. 19, 2011 and German Patent Application No. 10 2011 116 262.7, filed Oct. 19, 2011, both of which are hereby incorporated by reference in their entireties.

FIELD OF INVENTION

The present invention relates to a method for retrograde filling of a line for adding a medical solution, i.e. a solution used in medicine, the line branching off a return line of an extracorporeal blood circuit, e.g., a calcium line. Furthermore, the present invention relates to a control device, as well as a blood or plasma treatment apparatus with at least one control device according to the present invention. Furthermore, the present invention relates to a digital storage medium, a computer program product, as well as a computer program.

BACKGROUND OF INVENTION

Extracorporeal blood circuits for conducting blood outside the patient's body during a blood purification process are known from practice. Such blood circuits are filled with a priming solution before the beginning of the treatment. This filling is known as priming the blood circuit. Inter alia, it serves to displace air which is still present in the blood circuit before the treatment by utilization of a physiologically tolerated liquid or solution in order to prevent an introduction of this air into the vascular system of the patient during and in particular at the beginning of the blood treatment.

If the extracorporeal blood circuit comprises a line for adding a medical solution, for example a calcium-containing solution (here generally denoted as line for adding a medical solution or as calcium line, i.e. a line which is provided for adding or for exclusively adding calcium or calcium solution into an extracorporeal blood circuit), this line also has to be primed before the beginning of the treatment, at least, however, before its actual use.

One object of the present invention is to propose a method for priming a line for adding a medical solution, in particular a calcium line.

All advantages that are achievable by utilization of the method according to the present invention may in certain embodiments according to the present invention undiminishedly also be achieved by utilization of the apparatuses according to the present invention.

Thus, according to the present invention, a method for priming and/or filling and/or flushing a line for adding a medical solution, and in particular a calcium line, which branches off a return line of an extracorporeal blood circuit is proposed, and which is connected in fluid communication with it at a connection point or which joins it. Hereafter, the terms "line for adding a medical solution" and "calcium line" are used in parallel, whereby to simplify matters there is also only mention of a calcium line even if the explanation made hereto also applies to a line which is not provided or used for adding calcium, as is recognizable for the person skilled in the art. Herewith, it is clarified that whenever there is mention of a calcium line, this term is also replaceable by the more general term "line for adding a medical solution". The use of the term "calcium line" is not intended to restrict the present invention hereto. A calcium line is rather only one embodiment of the line according to the present invention for adding a medical solution, e.g., a drug solution, a volume replacement solution, and so on. The term "solution" is hereby in some embodiments according to the present invention to be understood as an arbitrary fluid which contains solid or dissolved components, i.e. also suspensions, emulsions, and the like. Also the objects which are denoted here as calcium solution container, calcium solution connector, calcium drip chamber, calcium pump and the like are not restricted to their use in connection with calcium or calcium solution. Here also, "calcium" is replaceable with any suitable medical solution. This is also encompassed by the present invention.

The method encompasses retrograde priming of the calcium line via the return line of the extracorporeal blood circuit with a priming solution. In doing so, the retrograde priming takes place while the extracorporeal blood circuit is primed, which is carried out by use of a blood or plasma treatment apparatus such as for example an apheresis apparatus, hemodialysis apparatus, hemofiltration apparatus, hemodiafiltration apparatus, and so on.

The control device according to the present invention is provided, set up, programmed and/or configured for controlling or regulating an apparatus for or during execution of the method according to the present invention.

The blood or plasma treatment apparatus according to the present invention comprises at least one control device according to the present invention and/or is provided and/or set up for executing the method according to the present invention. In certain embodiments, it comprises or is connected in operative and/or signal connection each with devices which are required for this purpose.

The digital storage medium according to the present invention, in particular in the form of a disk, CD or DVD, with electronically readable control signals may interact with a programmable computer system such that the mechanical or machine steps of the method according to the present invention are prompted.

The computer program product according to the present invention comprises a program code saved on a machine-readable storage device for prompting the mechanical or machine steps of the method according to the present invention when the computer program product runs on a computer.

The term "machine-readable storage device", as used herein, denotes in certain embodiments of the present invention a storage device which contains data or information which is interpretable by software and/or hardware. The storage device may be a data storage device such as a disk, a CD, DVD, a USB stick, a flashcard, an SD card and the like.

The computer program according to the present invention comprises a program code for prompting the mechanical or machine steps of the method according to the present invention when the computer program runs on a computer.

It applies to the digital storage medium, the computer program product according to the present invention and the computer program according to the present invention that all or some of the mechanically executed steps of the method according to the present invention are prompted.

In all of the following embodiments, the use of the expression "may be" or "may have" and so on, is to be understood synonymously with "preferably is" or "preferably has", respectively, and so on, and is intended to illustrate an embodiment according to the present invention.

Advantageous developments of the present invention are each subject of dependent claims and embodiments.

Embodiments according to the present invention may comprise one or more of the features named hereafter.

In certain embodiments according to the present invention of the method, the return line is provided for returning a bodily fluid which was extracorporeally treated into the vascular system of the treated patient. In some embodiments according to the present invention, the return line is the venous patient line.

The blood circuit serves in some embodiments according to the present invention to extracorporeally conduct blood such as whole blood or components hereof, but also other bodily fluids, such as plasma.

In some embodiments according to the present invention, "retrograde" is the direction of flow within the calcium line, in which a fluid flows in opposite direction of the flow direction (the anterograde flow direction), in which calcium flows through the calcium line when it is introduced into the extracorporeal blood circuit out of a calcium source such as a calcium solution container or calcium bag and through the calcium line during or towards the end of the treatment of the patient.

"Retrograde priming or filling of a calcium line" means in some embodiments according to the present invention filling the calcium line in a direction towards a calcium solution container (rather than away from it), and/or towards a point at which the calcium solution container is or would be provided in its normal or intended use or with utilization of the calcium line with reference to the same.

In certain embodiments according to the present invention, retrograde priming takes place via a detachable or undetachable connection section, by utilization of which the calcium line is or will be connected with the return line.

In certain embodiments according to the present invention, the priming solution is an arbitrary liquid which is used or normally used or is known as being usable for priming an extracorporeal blood circuit, for example a physiological NaCl solution, dialyzing liquid, substitute or the like.

In some embodiments of the method according to the present invention, the calcium line is detachably or undetachably connected in fluid communication with the return line of the extracorporeal blood circuit of a blood or plasma treatment apparatus by utilization of a connection section, for example a T-piece.

In some embodiments according to the present invention, the method encompasses non-inserting, detaching or removing or separating a pump tube section of the calcium line out of or from a calcium pump (hereafter also summarized as "detaching").

Non-inserting or detaching takes place in certain embodiments according to the present invention before the beginning of priming the extracorporeal blood circuit and/or before the completion of priming the extracorporeal blood circuit.

In certain embodiments according to the present invention, the method encompasses disrupting, modifying (in the sense of changing or varying) or ending the retrograde priming of the calcium line when, if, as soon as or after a predetermined detection level of the priming solution in a calcium drip chamber which is arranged in or at the calcium line, is or was reached and/or detected.

The method according to the present invention encompasses in some embodiments disrupting or ending retrograde priming of the calcium line, when, if, as soon as or after a predetermined detection level of the priming solution in the calcium drip chamber is or was reached or and/or detected.

Reaching the predetermined detection level is in some embodiments according to the present invention recognized by a calcium drip and level detector device which is arranged at the drip chamber.

In some embodiments according to the present invention, reaching the predetermined detection level is automatically recognized or in an automated way.

In certain embodiments according to the present invention, the method additionally encompasses the further filling of the calcium drip chamber with the priming solution, namely by an additional, predetermined volume of the priming solution, after the predetermined detection level is or was reached and/or detected. The volume of this priming solution may be, e.g., 3 ml. The volume may, however, deviate from this, and it may depend on the kind and type of the utilized elements or components. This way, a suitable or desired after-priming level of the priming solution in the calcium drip chamber is also ensured beyond the time at which the pump tube section is inserted into the calcium pump. Such inserting effects a dropping of the level of liquid in the calcium drip chamber. This may be completely or partially compensated or overcompensated in the manner as described here.

In some embodiments according to the present invention, the method encompasses detecting a predetermined detection level in the calcium drip chamber.

The method according to the present invention additionally encompasses in certain embodiments inserting the pump tube section into the calcium pump.

In some embodiments according to the present invention, the insertion of the pump tube section into the calcium pump takes place automatically. Corresponding devices, and preferably also devices for their automatic starting, may according to the present invention be provided at or connected with the blood or plasma treatment apparatus.

In certain embodiments according to the present invention, the insertion of the pump tube section into the calcium pump takes place after the predetermined detection level of the priming solution is or was reached and/or detected in the calcium drip chamber.

The method according to the present invention encompasses in some embodiments additionally changing the flow—or the flow rate of the priming solution through the return line—by utilization of a throttle device, a flow disruption device or a clamping device (which herein are for simplification in short denoted as clamping devices without restricting them to a device with an explicit clamping effect), which is arranged at the return line downstream from the connection section or downstream from a connection spot to the line for adding a medical solution, in particular to the calcium line.

If the predetermined detection level—or the after-priming level—in the calcium drip chamber is not reached during regular priming, in certain embodiments according to the present invention, a flow of liquid within the return line downstream from the connection point between the return line and the calcium line is manually or automatically throttled or stopped by utilization of the clamping device. This takes place, e.g., by engaging the clamping device. A corresponding request may be issued to the user, for example acoustically, optically, by utilization of a display, and so on. Throttling, limiting or stopping may alternatively take place automatically, for example after a suitable sensor signal by a provided sensor was received. Such throttling, clamping or the like may of course also take place by default and—independently hereof—also without a request.

In certain embodiments, the blood or plasma treatment apparatus according to the present invention comprises at least one calcium drip and level detector device. It may be designed for detecting a level of liquid in the drip chamber of the calcium line of the extracorporeal blood circuit.

In certain embodiments according to the present invention, the blood or plasma treatment apparatus comprises a device for inserting the pump tube section into the calcium pump.

In some embodiments according to the present invention, the blood or plasma treatment apparatus according to the present invention is embodied as an apheresis apparatus, hemodialysis apparatus, hemodiafiltration apparatus, hemofiltration apparatus or a combination thereof.

Some or all embodiments according to the present invention may comprise one, more or all of the advantages named above and/or hereafter.

It is known from practice that in plasma or blood treatments a substitution of calcium may be required regularly, for example, if an anticoagulation with citrate was carried out. Whether such a substitution will actually be required cannot always be reliably assessed in the run-up to the treatment. It is thus desirable to only open, e.g., a calcium solution container (for example, a bag with calcium solution) in case of need, and otherwise leave it preferably unopened in order to be able to use it in a later occurring blood or plasma treatment, if a calcium substitution is not required. This applies in particular in light of the fact that holding and storing such a calcium solution container is connected with effort and costs, just as its disposal. The latter applies in particular to the acquisition of such a container; its contents are expensive.

However, if the calcium solution container has to be used in the treatment, for example due to an uprising hypercalcemy or a recognized citrate incompatibility, the calcium line has to be reliably primed and thus emptied of air in order to prevent embolisms before the calcium solution is introduced.

Calcium solution containers are usually connected with the extracorporeal blood circuit directly at the return connector of the extracorporeal blood circuit by utilization of the calcium line, for example in order to prevent the introduced calcium from being filtered, furthermore, as the addition of calcium is particularly useful directly before the blood is returned to the vascular system of the patient. No check of the extracorporeal blood circuit for the presence of trapped air is carried out from this point on. The present invention advantageously remedies the situation by proposing a filling of the calcium line including monitoring the result of priming even before the beginning of the treatment in order to prevent the risk of an air embolism.

Another advantage according to the present invention is that in the event that during preparation of the extracorporeal blood circuit it is unknown whether calcium solution will be required at all (i.e. in the event of initially unknown requirement), the expensive calcium solution of the calcium solution container is not used for filling the calcium line, for example by utilization of anterograde filling, as is known in the context of attaching infusions. Rather, priming is carried out by utilization of cheap priming solution.

Priming according to the present invention advantageously takes place automatically. Manually attaching the calcium line to, e.g., a source of a priming solution, subsequent detaching of the calcium line from the source of a priming solution, and connecting the calcium line with the blood circuit may advantageously be omitted.

By non-inserting or detaching the pump tube section of the calcium line from a calcium pump, an unhindered flow through the pump tube section may advantageously be ensured. A possibly occluding effect of the calcium pump can be avoided which may enable priming in the first place or lead to a more thorough priming.

By non-inserting or detaching, filling the calcium line may possibly advantageously take place just by utilization of gravity or by utilization of the principle of communicating vessels.

When inserting the pump tube section into the calcium pump, the level of liquid advantageously drops to or just above the predetermined detection level at most due to the additionally added volume of priming solution; a level thus remains the same in the calcium drip chamber, as is permanently recognizable for the user.

BRIEF DESCRIPTION OF THE DRAWINGS

Hereafter, the present invention is exemplarily described with reference to the appended figures in which identical reference numerals refer to same or similar components. In the in part highly simplified figures it applies that.

DETAILED DESCRIPTION

Figure 1:
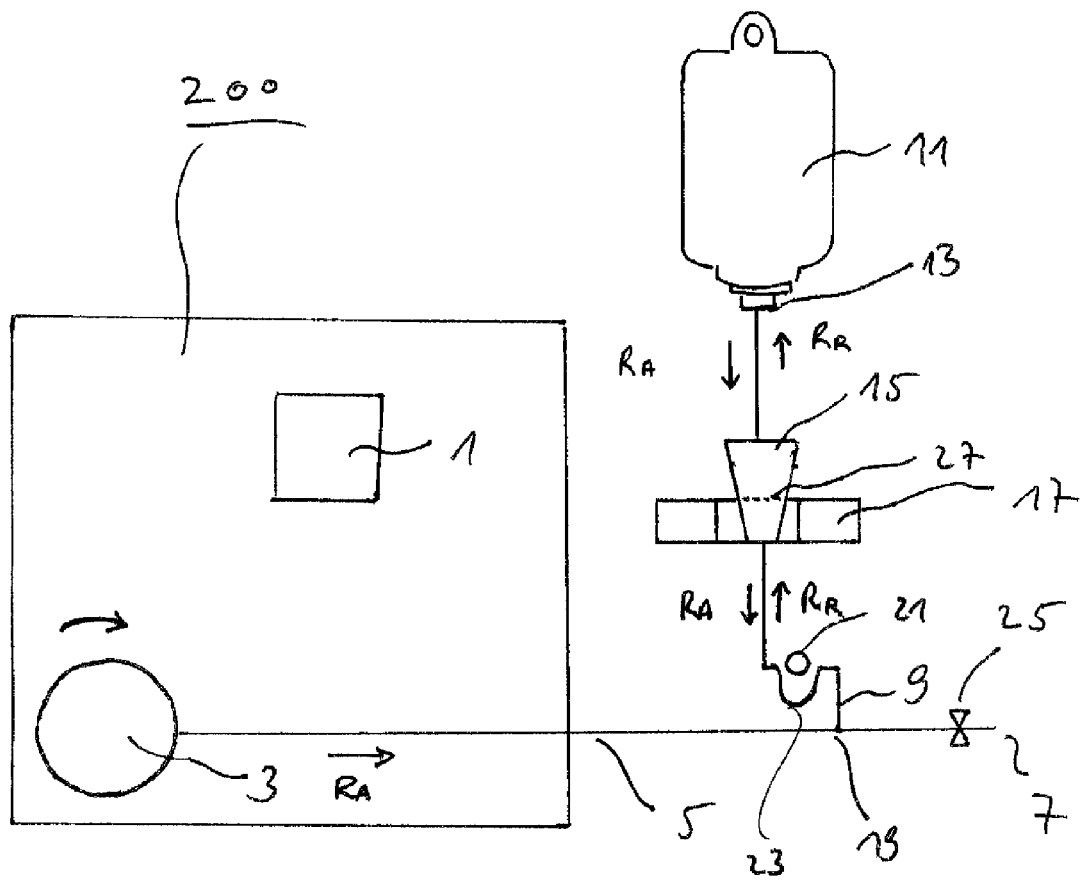
FIG. 1 shows a schematically simplified arrangement for executing an embodiment of the method according to the present invention in a first method step thereof.

FIG. 1 shows a schematically simplified blood circuit 100 which is inserted in a section of a blood or plasma treatment apparatus 200 by which the method according to the present invention takes place.

The section of the blood or plasma treatment apparatus 200 encompasses in the embodiment as illustrated here a blood pump 3 by which the blood circuit 100 is filled with priming solution for its priming in addition to a control device 1 according to the present invention.

The blood circuit 100, which in FIG. 1 is only illustrated in parts hereof, encompasses a return line 5 (also denoted as venous line) with a return connector 7 (also denoted as venous patient connector) for returning blood to the patient, who is not illustrated here, during the blood treatment. A calcium line 9 as an example of a line for adding a medical solution which is or can be fed out of the calcium solution container 11 with which it is connected by a calcium solution connector 13 or will be connected in case of need is in fluid connection with the return line 5. The calcium solution connector 13 may be embodied as or comprise a spike. The calcium solution connector 13 may be embodied as or comprise a ventilation device.

The calcium line 9 comprises a calcium drip chamber 15 and is inserted in or arranged at a calcium drip and level detector device 17 of the blood or plasma treatment apparatus 200, in particular in the area of the calcium drip chamber 15. The calcium line 9 is connected in unhindered fluid connection with the return line 5 at a connection point with a connection section 19.

Another section of the calcium line 9, which is arranged in or at a calcium pump 21 of the plasma or blood treatment apparatus 200, is denoted as pump tube section 23. The pump tube section 23 is in FIG. 1 not inserted in the calcium pump 21; it rather hangs freely or loosely. Its lumen is in this state not narrowed by the calcium pump 21.

The calcium solution which is stored in the calcium solution container 11 is only used in case of need.

When priming the blood circuit 100, the priming solution is anterogradely, i.e. in the direction of the arrows RA, through the return line 5, conveyed along the return line 5 via the blood pump 3 of the blood or plasma treatment apparatus 100. At the connection section 19, it retrogradely enters the calcium line 9 and flows in the direction towards the calcium solution container 11. The calcium line 9 is thus retrogradely filled in the direction of the arrows RR.

Filling the calcium line 9 takes place in retrograde direction according to the present invention, as described above, and along the arrows $R_R$ in FIG. 1. The opposite direction, denoted as anterograde direction, is illustrated in FIG. 1 through the arrows $R_A$. "Anterograde" thus denotes in contrast hereto the flow direction of the calcium solution originating from the calcium solution container 11 to the connection section 19.

Priming or filling the calcium line 9 thus takes place during priming of the rest of the blood circuit 100 or in the same step. It is carried out by utilization of the blood or plasma treatment apparatus 100, in particular before the end or completion of the priming procedure of the blood circuit 100. Priming takes place using the priming solution, with which also the blood circuit 100 was primed, and it takes place in retrograde direction, as with the calcium line 9.

When the calcium line 9 is retrogradely filled or primed, it is possible that the priming solution flows within the calcium line 9 just by utilization of gravity or by utilization of the principle of communicating tubes or vessels. Alternatively or supportively, the priming solution may be conveyed by use of a conveying pump—such as, for example, the blood pump 3 or a calcium pump 21 which conveys in reverse.

The pump tube section 23 of the calcium line 9 is in some embodiments according to the present invention during or at the beginning of priming, which for example takes place by use of 0.9% NaCl solution, not connected with or inserted in the calcium pump 21, at least not before priming of the calcium line 9 is also initially completed, disrupted or modified. This way, an unhindered flow of the liquid through the calcium line 9 is ensured.

In doing so, the pump tube section 23 can be held at the calcium pump 21, in particular a holding apparatus of the calcium pump 21, by utilization of a clip, whereby or while the pump tube section 23 is not inserted in the calcium pump 21.

For the approach as described above for priming the calcium line 9, escaping of air from the calcium line 9 is enabled, for example via the calcium solution connector 13, or by utilization of an air separator which is not shown here and as is known from the state of the art, and/or by leaving the connection of the calcium line 9 with the calcium solution container 11 open.

Only in the case of need, for example if a hypercalcemy of the patient occurs, the calcium solution container 11 is then connected to the calcium line 9 by utilization of the calcium solution connector 13. The calcium solution container 11 is only opened or started in the case of need. If a calcium substitution is not required, the calcium solution container stays untouched and can be used in a later occurring treatment session.

A clamping device 25 may be closed during filling of the calcium line 9. Thus, reaching a predetermined detection level 27 (illustrated with dashed line) in the calcium drip chamber 15 can be accelerated.

Filling the calcium line 9 is automatically or manually stopped when the predetermined detection level 27 is reached.

To ensure a desired after-priming level 31 (see FIG. 3), the calcium line 9 is filled with a predetermined volume of liquid. In the calcium drip chamber 15, a level 29 is thus reached which is above the detection level 27. This is shown in FIG. 2.

Figure 2:
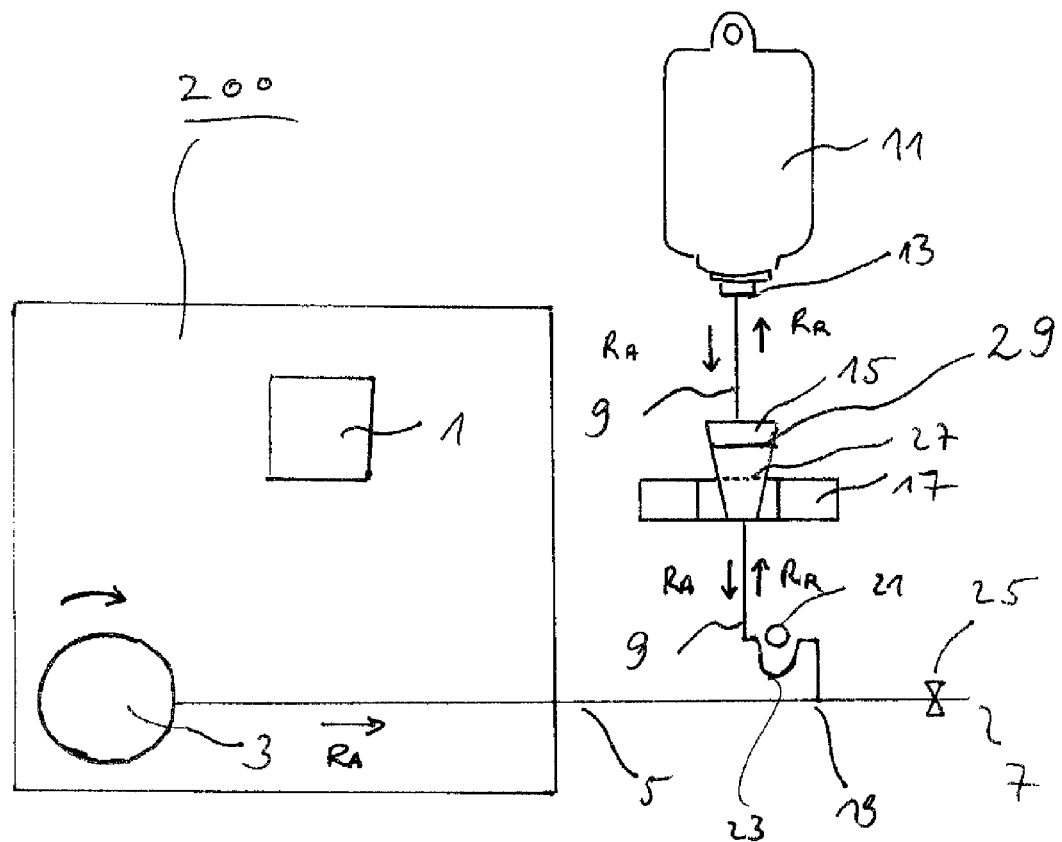
FIG. 2 shows the arrangement of FIG. 1 in a subsequent second method step.
Figure 3:
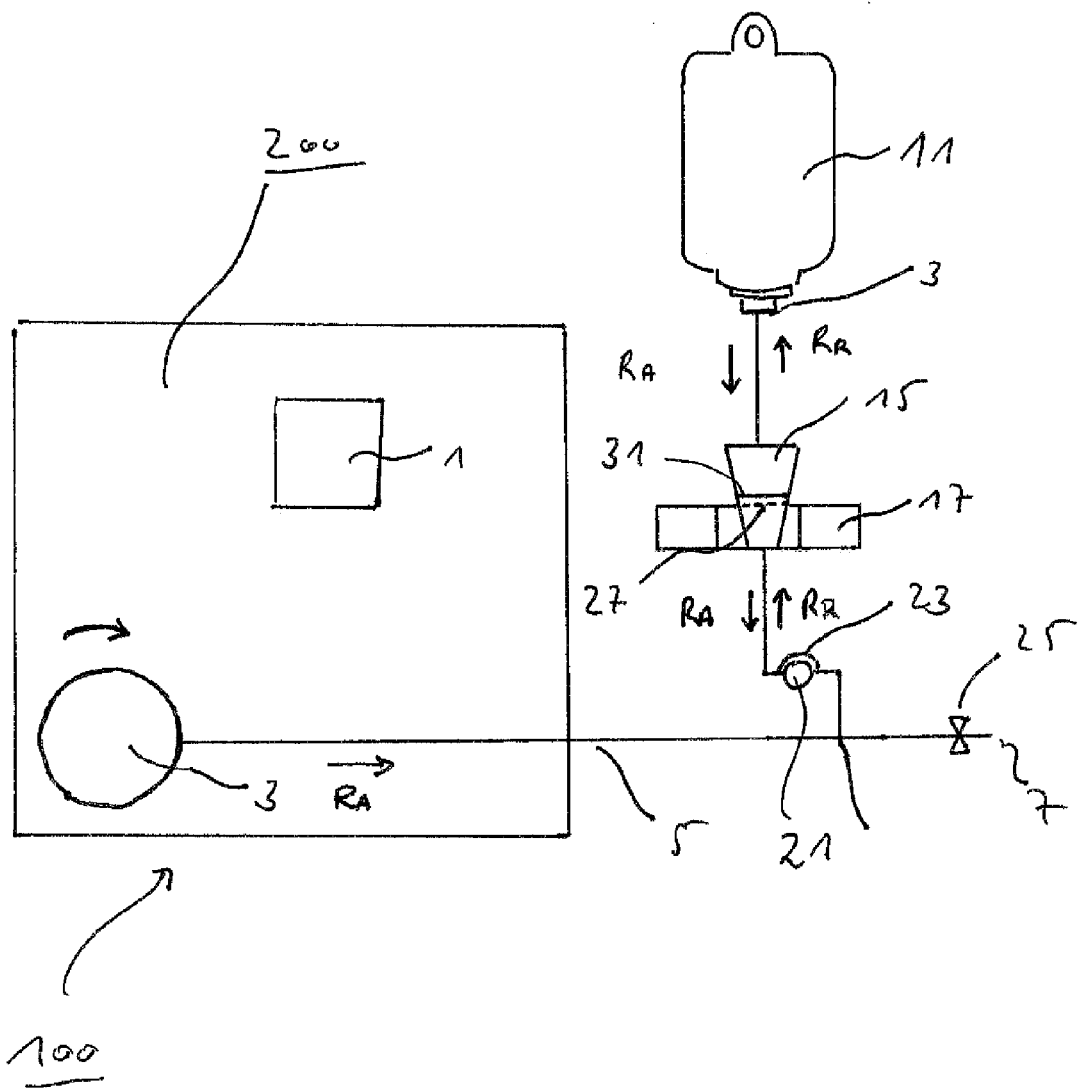
FIG. 3 shows the arrangement of FIG. 2 in a subsequent third method step.

FIG. 3 shows that the pump tube section 23 meanwhile is inserted into the calcium pump 21, it is not hanging any more—other than in the first and second method steps as shown in FIG. 1 and FIG. 2. Due to the insertion, the level 29 in the calcium drip chamber 15 (see FIG. 2) has dropped to the after-priming level 31, a level which is always recognizable for the user and thus easy to monitor. This after-priming level 31 is above the predetermined detection level 27. The user may thus check with one glance whether the calcium line 9 is available and sufficiently primed.

REFERENCE NUMERAL LIST 1 control device
3 blood pump
5 return line
7 return connector to the patient
9 calcium line
11 calcium solution container
13 calcium solution connector
15 calcium drip chamber of the calcium drip and level detector device 17
17 calcium drip and level detector device
19 connection section
21 calcium pump
23 pump tube section
25 clamping device at the return connector 7
27 predetermined detection level
29 level
31 after-priming level
100 extracorporeal blood circuit
200 blood or plasma treatment apparatus
RA anterograde direction
RR retrograde direction

What is claimed is:

1. A method for priming a line for adding a medical solution, said line for adding the medical solution branching off a venous line of an extracorporeal blood circuit, the method comprising the step of:
   retrograde priming of the line for adding the medical solution via the venous line of the extracorporeal blood circuit with a priming solution,
   wherein the retrograde priming takes place while the extracorporeal blood circuit is primed via a blood or plasma treatment apparatus,
   wherein the line for adding the medical solution is a calcium line.

2. The method according to claim 1, wherein the calcium line is in fluid communication with the venous line via a detachable connection section.

3. The method according to claim 1, further comprising the step of:
   detaching a pump tube section of the calcium line from a pump.

4. The method according to claim 1, further comprising the step of:
   at least one of disrupting, modifying or stopping the retrograde priming of the calcium line if a predetermined detection level of the priming solution is at least one of reached or detected in a drip chamber which is arranged in or at the calcium line.

5. The method according to claim 1, further comprising the step of:
   at least one of disrupting, modifying or stopping the retrograde priming of the calcium line if a predetermined detection level of the priming solution is at least one of reached or detected in a drip chamber which is arranged in or at the calcium line, wherein the predetermined detection level is detected by a drip and level detector device which is arranged at the drip chamber.

6. The method according to claim 5, further comprising the step of:
further filling the drip chamber with the priming solution by a predetermined volume of priming solution after the predetermined detection level is at least one of reached or detected by the drip and level detector device.

7. The method according to claim 3, further comprising the step of:
inserting the pump tube section into the pump.

8. The method according to claim 2, further comprising the step of:
changing the flow or the flow rate of the priming solution through the venous line via a clamping device which is arranged at the venous line downstream from the connection section or downstream from a connection spot to the calcium line.

9. A system for controlling or regulating a method for priming a line for adding a medical solution, said line for adding the medical solution branching off a venous line of an extracorporeal blood circuit, wherein said line for adding the medical solution is a calcium line, said system comprising a control device configured to control or regulate the method according to claim 1.

10. The system of claim 9, wherein the system further comprises:
a blood or plasma treatment apparatus comprising said control device.

11. The system of claim 10, wherein the blood or plasma treatment apparatus further comprises:
at least one calcium drip and level detector device configured to detect a level of liquid in at least one calcium drip chamber of the calcium line which is connected with the blood or plasma treatment apparatus.

12. The system of claim 10, wherein the blood or plasma treatment apparatus is selected from the group consisting of: an apheresis apparatus, a hemodialysis apparatus, a hemofiltration apparatus, and a hemodiafiltration apparatus.

13. A non-transitory computer-readable storage medium with an executable program stored thereon, wherein the program instructs a programmable computer system so as to execute the steps of the method according to claim 1.

* * * * *